United States Patent [19]

Schmierer et al.

[11] Patent Number: 4,755,213
[45] Date of Patent: Jul. 5, 1988

[54] 1-PHENYLIMIDAZOLECARBOXYLIC ACID AMIDES AND THEIR USE AS GROWTH REGULATORS

[75] Inventors: Roland Schmierer, Todtenweis; Reinhard Handte, Gablingen; Hilmar Mildenberger, Kelkheim; Helmut Bürstell, Frankfurt am Main, all of Fed. Rep. of Germany

[73] Assignee: Hoechst Aktiengesellschaft, Frankfurt am Main, Fed. Rep. of Germany

[21] Appl. No.: 24,357

[22] Filed: Mar. 10, 1987

[30] Foreign Application Priority Data

Mar. 12, 1986 [DE] Fed. Rep. of Germany ....... 3608143

[51] Int. Cl.⁴ .................... A01N 43/50; C07D 233/90
[52] U.S. Cl. .......................................... 71/92; 548/343
[58] Field of Search ............................ 548/343; 71/92

[56] References Cited

FOREIGN PATENT DOCUMENTS 3217094 11/1983 Fed. Rep. of Germany ...... 548/343

OTHER PUBLICATIONS

March, J., *Advanced Organic Chemistry*, McGraw Hill, New York, 1968, pp. 335-339.

*Primary Examiner*—Richard A. Schwartz
*Attorney, Agent, or Firm*—Curtis, Morris & Safford

[57] ABSTRACT

The compounds of the formula (I)

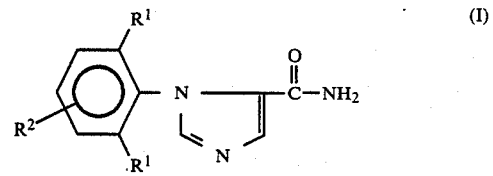

in which $R^1$ denotes $(C_1-C_3)$alkyl and $R^2$ denotes H, methyl or halogen, and salts thereof have excellent actions as plant growth regulators, in particular in rice crops.

5 Claims, No Drawings

1-PHENYLIMIDAZOLECARBOXYLIC ACID AMIDES AND THEIR USE AS GROWTH REGULATORS

1-Phenyl-imidazole-5-carboxylic acid derivatives and their use as fungicides, herbicides and plant growth regulators are known from German Pat. No. A-3,217,094.

These compounds have the general formula (A)

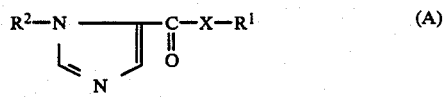

in which $R^1$ denotes H, phenyl, alkyl, alkenyl, both of which can be substituted by halogen, alkoxy or dialkylamino, a metal cation or ammonium, $R^2$ denotes a substituted phenyl radical and X denotes O, S or N, and in the case where X=N, two radicals $R^1$ are bonded to X.

It has now been found, surprisingly, that selected 1phenylimidazolecarboxylic acid amides which are not described in German Pat. No. A-3,217,094 have particularly intensive growth-regulating actions, especially in rice crops.

The present invention therefore relates to the compounds of the formula I

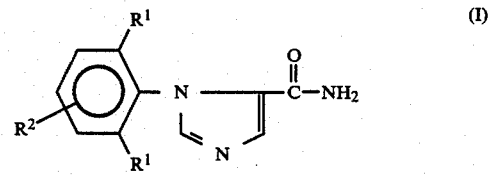

in which
the radicals $R^1$ independently of one another denote $(C_1-C_3)$alkyl and
$R^2$ denotes H, methyl or halogen, and salts thereof which can be used in agriculture.
$R^1$ denotes, in particular, ethyl and
$R^2$ denotes, in particular, hydrogen.

The invention furthermore relates to a process for the preparation of the compounds of the formula I, which comprises subjecting a compound of the formula II

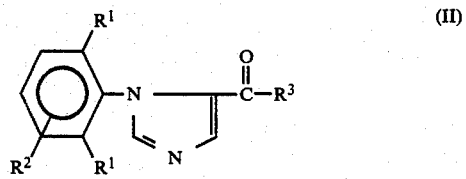

in which $R^1$ and $R^2$ have the abovementioned meanings, $R^3$ denotes a radical of the formula $-O-R^4$, $-OH$, Cl,

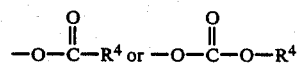

and $R^4$ denotes $(C_1-C_8)$alkyl, to ammonolysis and, if desired, converting the resulting compounds into their salts.

The ammonolyses can be carried out by generally customary methods, for example reaction of the compounds II where $R^3=OR^4$ with ammonia or with substances which release ammonia when heated, such as urea, formamide or $(NH_4)_2CO_3$, if appropriate under pressure, at temperatures between 100° and 250° C. (for example Houben-Weyl VIII, page 656 et seq.); or by conversion of the compounds of the formula II in which $R^3=OH$ into an ammonium salt, which is then decomposed by heat. The ammonium salt can be prepared, for example, by reaction of the acids with ammonia or with the abovementioned substances which liberate ammonia (for example Houben-Weyl VIII, page 645 et seq.); or by reaction of the compounds of the formula II in which $R^3=Cl$,

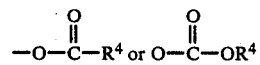

with aqueous or gaseous ammonia, if appropriate in the presence of an inert solvent, at 0° to 100° C. (for example Organikum, 1973, page 453 et seq.).

The salts of the formula I which can be used for agriculture are imidazolium salts; these can be prepared by known processes with strong acids, such as, for example, hydrochloric acid, sulfuric acid, methanesulfonic acid, chloroethanephosphonic acid or trichloroacetic acid, at a pH of ≦2.

Typical growth-regulating effects which can even start at low dosages can be achieved with the compounds according to the invention. They intervene in the endogenous metabolism of the plant in a regulatory manner and can therefore be used for controlled influencing of plant contents, for increasing the yield and for facilitating harvesting and compressing growth. They are moreover also suitable for general control and inhibition of undesirable vegetative growth, without thereby destroying the plants. Inhibition of vegetative growth is of great importance in many mono- and dicotyledon crops, since lodging can thereby be reduced or completely prevented. The growth-regulatory action of the compounds as growth inhibitors in rice is to be singled out in particular.

The invention also relates to agents which regulate plant growth and which are distinguished by an effective content of at least one of the compounds according to the invention.

The compounds according to the invention can be used, if appropriate as a mixture with other active components, as wettable powders, emulsifiable concentrates, solutions for spraying, dusts, dispersions, granules or microgranules in the customary formulations.

Wettable powders are preparations which are uniformly dispersible in water and which, in addition to the active compound(s), also contain, if appropriate, a diluent or inert substance or wetting agent, such as polyoxyethylated fatty alcohols and alkyl- or alkylphenylsulfonates, and/or a dispersing auxiliary, such as sodium ligninsulfonate, sodium 2,2'-dinaphthylmethane-6,6'-disulfonate, sodium dibutylnaphthalenesulfonate or sodium oleoylmethyltauride. They are prepared in the customary manner, for example by grinding and mixing the components.

Emulsifiable concentrates can be prepared, for example, by dissolving the active compounds in an inert organic solvent, such as butanol, cyclohexanone, dimethylformamide, xylene or higher-boiling aromatics or aliphatic or cycloaliphatic hydrocarbons, with the addition of one or more emulsifiers. In the case of liquid active compounds, it is also possible for all or some of the solvent content to be dispensed with. Examples of emulsifiers which can be used are: calcium alkyl-arylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, fatty alcohol-propylene oxide condensation products, alkyl polyglycol ethers, sorbitan fatty acid esters, polyoxyethylene sorbitan acid esters or polyoxyethylene sorbitol esters.

Dusts can be obtained by grinding the active compounds with finely divided solid substances, for example talc or natural clays, such as kaolin, bentonite, pyrophillite or diatomaceous earth. Granules can be prepared either by spraying the active compounds onto an adsorbent granulated inert material or by applying active compound concentrates to the surface of carriers, such as sand, kaolinite or a granular inert material, by means of binders, for example polyvinyl alcohol, sodium polyacrylate or mineral oils. It is also possible for suitable active compounds to be granulated in the customary manner for the preparation of fertilizer granules—if desired as a mixture with fertilizers.

The active compound concentration in wettable powders is about 5 to 90% by weight, the remainder to make up to 100% by weight consisting of the customary formulation constituents. The active compound concentration in emulsifiable concentrates can be about 3 to 80% by weight. Dust-like formulations usually contain 0.025 to 20% by weight of active compound(s), and sprayable solutions contain about 2 to 20% by weight. In the case of granules, the active compound content depends in part on whether the active compound is in liquid or solid form and on what granulation auxiliaries, fillers and the like are used. In addition, the active compound formulations according to the invention contain, if appropriate, the particular customary adhesives, wetting agents, dispersing agents, emulsifiers, penetration agents, solvents, fillers or carriers.

For use, the concentrates in the commercially available form are diluted, if appropriate, in the customary manner, for example by means of water in the case of wettable powders, emulsifiable concentrates, dispersions and in some cases also microgranules. Dust-like and granular formulations and sprayable solutions are usually not diluted further with additional inert substances before use.

The amount of compounds according to the invention applied in general varies between 0.02 and 2.5 kg of active substance per hectare, preferably 0.05 to 1.5 kg/ha. The compounds according to the invention, in particular the compounds mentioned in the examples, can also advantageously be combined, if appropriate, with known growth regulators when used in practice. Such known growth regulators are the compounds of the formula

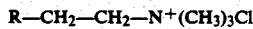

in which R denotes OH or Cl (common name chlormequat for R=Cl), and furthermore N,N-dimethylpiperidinium chloride (mepiquat chloride), α-cyclopropyl-4-methoxy-α-(pyrimidin-5-yl)benzyl alcohol (ancymidol), (3aα,4β,4aα,6aα,7β, 7aα)-1-(4-chlorophenyl)-3a, 4,4a, 6a, 7,7a-hexahydro-4,7-methano-1H-[1,2]diazeto[3,4-f]benzotriazole (tetcylacis), succinic acid mono-2,2-dimethylhydrazide (diaminoazide), 6-hydroxy-2H-pyridazin-3-one (maleic anhydride), 2-chloro-9-hydroxy-9H-fluorene-9-carboxylic acid (chlorflurenol), 5'-(trifluoromethanesulfonamido)acetate 2',4'-xylidide (mefluidide) and 2-chloroethylphosphonic acid (ethephon).

The growth-regulatory actions of these compounds are described in the Plant Growth Regulator Handbook of the Plant Growth Regulator Working Group 2nd edition 1981.

Instead of the compounds chlormequat or mepiquat chloride, in principle comparable salts which contain another customary anion, such as bromide, nitrate or sulfate, instead of the chloride ion can also be employed.

Combinations of the compounds I, in particular those of Example 1 * r salts thereof, with ethephon can also advantageously be used in crops in a temperate climate, such as in Cruciferae (for example rape) or Gramineae (for example barley).

The combinations can also be in the form of mixed formulations of the components, which are then used in the customary manner as a dilution with water; or they can be prepared as so-called tank mixes by common dilution of the separately formulated components with water; there is also the possibility of using the components in succession, that is to say the components are applied in individual formulations.

The compounds of the general formula (I) can also be combined with natural or vegetable hormones, such as auxins or cytokins.

FORMULATION EXAMPLES

Example 1

A dust is obtained (a) by mixing 10 PW$^{(1)}$ of active compound with 90 PW of talc or another inert substance and comminuting the mixture in an impact mill, or (b) homogenizing 60 PW of active compound, 35 PW of talc and 5 PW of adhesive (for example a polysaccharide such as (R)Rhodopol from Rhône-Poulenc S.A.) in the same manner.

$^{(1)}$ PW=parts by weight

Example 2

A wettable powder which is readily dispersible in water is obtained by mixing 25 PW of active compound, 64 PW of kaolin-containing quartz, as the inert substance, 10 PW of potassium lignin-sulfonate and 1 PW of sodium oleoylmethyltauride, as the wetting and dispersing auxiliary, and grinding the mixture in a pinned disk mill. A formulation with an active compound content of 5% can be composed as follows: 5% of active compound, 6% of a sulfonated naphthalene-formaldehyde condensate (for example (R)Dispersogen A from Hoechst AG), 2% of an Na salt of an alkylnaphthalenesulfonic acid (for example (R)Leonil DB from Hoechst AG), 5% of a mixture of polypropylene glycol and SiO$_2$ (for example (R) Acrotin 341 from Hoechst AG), 25% of a silicate (for example (R)Sipernat from Degussa AG) and 57% of kaolin type 1777.

Example 3

A dispersion concentrate which is readily dispersible in water is obtained by mixing 20 PW of active compound with 6 PW of an alkylphenol polyglycol ether (for example (R)Triton×207 from Rohm and Haas Co.), 3 PW of isotridecanol polyglycol ether (8 units of ethylene oxide) and 71 PW of paraffinic mineral oil (boiling range about 255° to more than 377° C.) and grinding the mixture to a fineness of less than 5 μm in a friction bead mill.

Example 4

An emulsifiable concentrate is obtained from 15 PW of active compound(s), 75 PW of cyclohexanone, as the solvent, and 10 PW of oxyethylated nonylphenol (10 units of ethylene oxide), as the emulsifier.

PW = parts by weight.

CHEMICAL EXAMPLES

Example 1

1-(2,6-Diethylphenyl)-imidazole-5-carboxamide 24.4 g (0.1 mol) of 1-(2,6-diethylphenyl)-imidazole-5carboxylic acid were added in portions to 36 g (0.3 mol) of thionyl chloride and 1 ml of dimethylformamide. After the addition, the mixture was heated at 80° C. until the evolution of gas had ended, and the solid residue was dried in vacuo and introduced in portions into 150 ml of ice-cold concentrated aqueous ammonia solution with thorough stirring. The mixture was stirred at room temperature for 1 hour; the precipitate was filtered off and dried. 20.2 g of 1-(2,6-diethylphenyl)-imidazole-5-carboxamide were obtained as a colorless solid of melting point 171°–171.5° C. (ethyl acetate/hexane); yield: 83% of theory.

Further examples are shown in Table 1.

TABLE 1

Imidazole-5-carboxamides

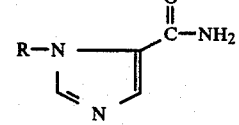

| Example No. | R | Melting point (°C.) |
|---|---|---|
| 2 | 2,6-Dimethyl-phenyl | |
| 3 | 2-Ethyl-6-methyl-phenyl | 150–154 |
| 4 | 2-Ethyl-6-isopropyl-phenyl | 198–203 |
| 5 | 2-Isopropyl-6-methyl-phenyl | |
| 6 | 2,6-Diisopropyl-phenyl | |
| 7 | 2,6-Diethyl-phenyl (hydrochloride) | Resin |
| 8 | 2,6-Diethyl-phenyl (chloroethane-phosphonate) | Resin |
| 9 | 2,6-Diethyl-3-methyl-phenyl | 147–151 |
| 10 | 2,6-Diethyl-4-methyl-phenyl | |
| 11 | 2,6-Diethyl-4-bromo-phenyl | |
| 12 | 2,6-Diethyl-3-chloro-phenyl | 188–193 |
| 13 | 2,6-Diethyl-phenyl (hydrogen sulfate) | 178 (decomp.) |
| 14 | 2,6-Diethyl-phenyl (methanesulfonate) | 182–186 |
| 15 | 2,6-Diethyl-phenyl (trichloroacetate) | 80 (decomp.) |

BIOLOGICAL EXAMPLES

Inhibition of growth in paddy rice

Rice plants were grown and in the stage of maximum tillering were treated with the compounds according to the invention and with a comparison compound from German Pat. No. A-3,217,094. The substances were both applied by spraying and also added directly to the water.

Three weeks after treatment, the additional growth of all the plants was measured and the inhibition of growth was calculated in % of the addition growth of the control plants. Attention was also paid to a possible phytotoxic action of the compounds. The inhibition of growth is determined as a percentage value, 100% denoting that growth has stopped and 0% denoting a growth corresponding to that of the untreated control plants.

TABLE 2

| Compounds according to Example No. | Use concentration (kg/ha) | Growth inhibition % | Phytotoxic action |
|---|---|---|---|
| 1 | 1.25 | 35 | no damage |
|   | 0.62 | 29 |   |
| 3 | 1.25 | 12 | damage |
|   | 0.62 | 7 | damage |
| 4 | 1.25 | 16 | no |
|   | 0.62 | 11 | damage |
| 7 | 1.25 | 32 | no |
|   | 0.62 | 27 | damage |
| 8 | 1.25 | 31 | no |
|   | 0.62 | 25 | damage |
| 13 | 1.25 | 29 | no |
|   | 0.62 | 24 | damage |
| 14 | 1.25 | 26 | no |
|   | 0.62 | 21 | damage |
| 15 | 1.25 | 27 | no |
|   | 0.62 | 20 | damage |
| A | 1.25 | 11 | no |
|   | 0.62 | 7 | damage |

We claim:
1. A compound of the formula I

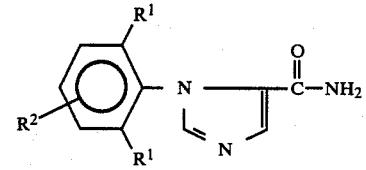

in which
the radicals $R^1$ independently of one another denote $(C_1-C_3)$alkyl and
$R^2$ denotes H, methyl or halogen, or an agriculturally acceptable salt thereof.

2. A compound of the formula I or a salt thereof, in which $R^2$ denotes H.

3. The compound 1-(2,6-diethylphenyl)-imidazole-5-carboxamide.

4. A plant growth-regulating agent comprising an effective amount of a compound of the formula (I) or a salt thereof as claimed in claim 1 in an inert carrier.

5. A method for regulating the growth of plants, which comprises applying an effective amount of a compound of the formula (I) as claimed in claim 1 to the plants or the cultivation areas.

* * * * *